(12) United States Patent
Plachta et al.

(10) Patent No.: US 12,343,523 B2
(45) Date of Patent: *Jul. 1, 2025

(54) IMPLANTABLE ELECTRODE ARRANGEMENT (71) Applicant: Neuroloop GmbH, Freiburg (DE)

(72) Inventors: Dennis Plachta, Voerstetten (DE); Mortimer Giehrtmuehlen, Freiburg (DE); Thomas Stieglitz, Freiburg (DE); Josef Zentner, Freiburg (DE)

(73) Assignee: NEUROLOOP GMBH, Freiburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,281

(22) Filed: Nov. 8, 2023

(65) Prior Publication Data
US 2024/0075281 A1  Mar. 7, 2024

Related U.S. Application Data (63) Continuation of application No. 15/517,903, filed as application No. PCT/EP2015/073129 on Oct. 7, 2015, now Pat. No. 11,850,419.

(30) Foreign Application Priority Data

Oct. 7, 2014  (DE) .......................... 102014014927.7

(51) Int. Cl.
A61N 1/05 (2006.01)
A61B 5/24 (2021.01)

(52) U.S. Cl.
CPC ............. A61N 1/0556 (2013.01); A61B 5/24 (2021.01); A61B 2562/066 (2013.01); A61B 2562/164 (2013.01)

(58) Field of Classification Search
CPC .. A61N 1/0556; A61B 5/24; A61B 2562/066; A61B 2562/164
See application file for complete search history.

(56) References Cited

U.S. PATENT DOCUMENTS 4,969,468 A * 11/1990 Byers ................. A61B 5/287
                                                        29/829
5,324,322 A    6/1994 Grill, Jr.
(Continued)

FOREIGN PATENT DOCUMENTS

DE      4433111      3/1996
DE      10020846     12/2001
(Continued)

OTHER PUBLICATIONS

International Search Report for PCT/EP2015/073129 mailed Jan. 8, 2016; English translation, 7 pages.
(Continued)

Primary Examiner — Adam Z Minchella
(74) Attorney, Agent, or Firm — Fitch, Even, Tabin & Flannery LLP (57) ABSTRACT An implantable electrode arrangement provides spatially-selective detection of neuronal electrical signals, which propagate along at least one nerve fiber contained in a nerve fascicle, and for selective electrical stimulation of the at least one nerve fiber, comprising a biocompatible carrier substrate, which has at least one carrier substrate region that can be placed around the nerve fascicle in a cuff and has a straight cylinder-shaped carrier substrate surface which faces the nerve fascicle in the implanted state. The carrier substrate surface has an axial extension and an extension oriented circumferentially in a direction and a first electrode arrangement attached thereto. The electrode arrangement comprises in an axial sequence, at least three first electrode structures with at least two first electrode surfaces arranged
(Continued)

in the circumferentially, and at least two spaced first electrode strips, displayed in the axial direction which extend circumferentially which are in a ring shape, which encloses the at least three electrode structures on both sides in the axial direction. The electrodes are connectable or are connected to a signal detector and generator.

31 Claims, 6 Drawing Sheets

(56) References Cited

U.S. PATENT DOCUMENTS

| | | | |
|---|---|---|---|
| 5,919,220 A | 7/1999 | Stieglitz | |
| 6,052,608 A * | 4/2000 | Young | A61N 1/0531 607/116 |
| 8,755,907 B2 * | 6/2014 | Kieval | A61N 1/36071 607/118 |
| 9,603,538 B2 * | 3/2017 | Fisher | A61N 1/3605 |
| 2003/0040785 A1 * | 2/2003 | Maschino | A61N 1/0556 607/118 |
| 2004/0024439 A1 * | 2/2004 | Riso | A61N 1/0556 607/116 |
| 2004/0243182 A1 * | 12/2004 | Cohen | A61N 1/36007 607/2 |
| 2004/0243208 A1 * | 12/2004 | Jordan | A61N 1/0553 607/117 |
| 2006/0004417 A1 | 1/2006 | Rossing | |
| 2006/0241697 A1 | 10/2006 | Libbus | |
| 2008/0103545 A1 * | 5/2008 | Bolea | A61N 1/0556 607/42 |
| 2011/0112591 A1 * | 5/2011 | Seymour | A61B 5/24 600/377 |
| 2014/0046407 A1 * | 2/2014 | Ben-Ezra | A61N 1/36053 607/72 |
| 2017/0319846 A1 | 11/2017 | Plachta | |

FOREIGN PATENT DOCUMENTS

| | | |
|---|---|---|
| DE | 60210928 | 5/2007 |
| EP | 2263745 | 12/2010 |
| WO | 9320887 | 10/1993 |
| WO | 2013150524 | 10/2013 |

OTHER PUBLICATIONS

Written Opinion of the International Searching Authority or PCT/EP2015/073129 mailed Jan. 8, 2016; English Translation submitted, 9 pages.

* cited by examiner

IMPLANTABLE ELECTRODE ARRANGEMENT

CROSS-REFERENCE TO RELATED APPLICATIONS

This application is a Continuation Application of Ser. No. 15/517,903, filed Apr. 7, 2017 which claims the benefit of International Application No. PCT/EP2015/073129 filed Oct. 7, 2015, and German Patent Application No. 102014014927.7, filed Oct. 7, 2014, which applications are incorporated herein by reference in their entirety.

BACKGROUND OF THE INVENTION

Field of the Invention

The invention relates to an implantable electrode arrangement for spatially-selective detection of neuronal electrical signals, which propagate along at least one nerve fiber contained in a nerve fascicle, and for selective electrical stimulation of the at least one selected nerve fiber, comprising a biocompatible carrier substrate, which has at least one carrier substrate region that can be placed around the nerve fascicle in a cuff and has a straight cylinder-shaped carrier substrate surface oriented facing the nerve fascicle in the implanted state, the carrier substrate surface has an axial extension and an extension oriented in the circumferential direction and a first electrode arrangement attached thereto. The first electrode arrangement comprises, in an axial sequence and spaced apart from one another, at least three first electrode structures with in each case at least two first electrode surfaces arranged in a manner distributed in the circumferential direction, and at least two first electrode strips, which are spaced apart from one another in the axial direction, extending in the circumferential direction and in each case assumes a ring shape The first electrode strips enclose the at least three electrode structures on both sides in the axial direction. The first electrode arrangement is connectable to a signal detector and generator, with the electrode arrangement being connected to the signal detector and generator by a separable electrical interface, for example in the form of a plug, or is directly, (non-separably) connected.

Description of the Prior Art

Arterial hypertension is a globally widespread, typical lifestyle disease, which threatens the life of millions of patients and at the same time places the health systems under great strain. Previously known therapeutic measures are based on the administration of blood-pressure-lowering drugs, such as ACE inhibitors, beta-blockers, etc. However, these have considerable side effects in addition to the desired blood-pressure-lowering effect, for example bradycardia, cardiac insufficiency, asthma attacks, etc. In addition, in spite of the development of new blood-pressure-lowering drugs, it is not possible to achieve adequate target blood pressure in up to 30% of all patients with corresponding medication. See the article by H. R. Black, et al., Principal Results of the Controlled Onset Verapamil Investigation of Cardiovascular End Points (Convince), TRIAL. Jama, 289 (16), pages 2073-2082), 2003.

Another therapeutic approach for combating high blood pressure is pursued in a study by the applicant published in the article by Dennis T. T. Plachta, Oscar Cota, Thomas Stieglitz, Mortimer Gierthmuehlen, "Selektive Ableitung und Stimulation für ein blutdrucksenkendes Implantat unter Verwendung von Vielkanal—Cuff-Elektroden" (Selective Discharge and Stimulation for a Blood Pressure-Lowering Implant with Use of Multi-Channel Cuff Electrodes", tm—Technisches Messen (Technical Measurement), 2013, vol. 80 (5), pages 163-172. The findings obtained on the basis of animal tests performed on rats establish the possibility of detecting neuronal electrical signals in a spatially resolved manner from a nerve fascicle portion of the vagus nerve by an electrode arrangement implanted at the nerve fascicle portion, and of applying electrical signals to selected nerve fibers for stimulation thereof for the purposes of a technically initiated blood pressure reduction. A vagus nerve stimulation of this type thus in principle has the potential to become established as an alternative for the treatment of therapy-resistant blood pressure.

The concept of selective vagus nerve stimulation is supported on experience gained in the case of neuromodulation therapy of severe forms of epilepsy, which therapy has been applied and established for many years and in which the vagus nerve is electrically stimulated as a whole with the aid of an implanted electrode arrangement so as to at least reduce the extent of imminent epileptic seizures in respect of their strength and duration; See F. Sidiqui, et al., "Cumulative Effect of Vagus Nerve Stimulators on Intractable Seizures Observed Over a Period of 3 years", Epilepsy and Behavior, 18(3), pages 299-302, 2010 and also T. Stieglitz, "Neuroprothetik und Neuromodulation-Forschungsansatze und klinische Praxis bei Therapie und Rehabilitation" (Neuroprosthetics and Neuromodulation—Research Approaches and Clinical Practice in Therapy and Rehabilitation), Bundesgesundheitsblatt—Gesundheitsforschung—Gesundheitsschutz (public health journal), 53(8), pages 783-790, 2010.

In contrast, for the chronic treatment of hypertension it is necessary to firstly localize the blood pressure-relevant fibers by way of measurement in order to then selectively electrically stimulate them suitably. In order to treat the vagus nerve as gently as possible by means of the implantation for application of an electrode arrangement and so as to cause minimal irritation to the epineurium of the vagus nerve, it is proposed in the cited article by Dennis T. T. Plachta et al. to use what is known as a cuff electrode, which can be attached to the vagus nerve extraneurally. This has the advantage of a relatively easy positioning of the cuff electrode along the vagus nerve and in addition enables a surgical intervention on the patient that is only slightly invasive and therefore can be performed in a gentle and quick manner.

Figures 2A, 2B:
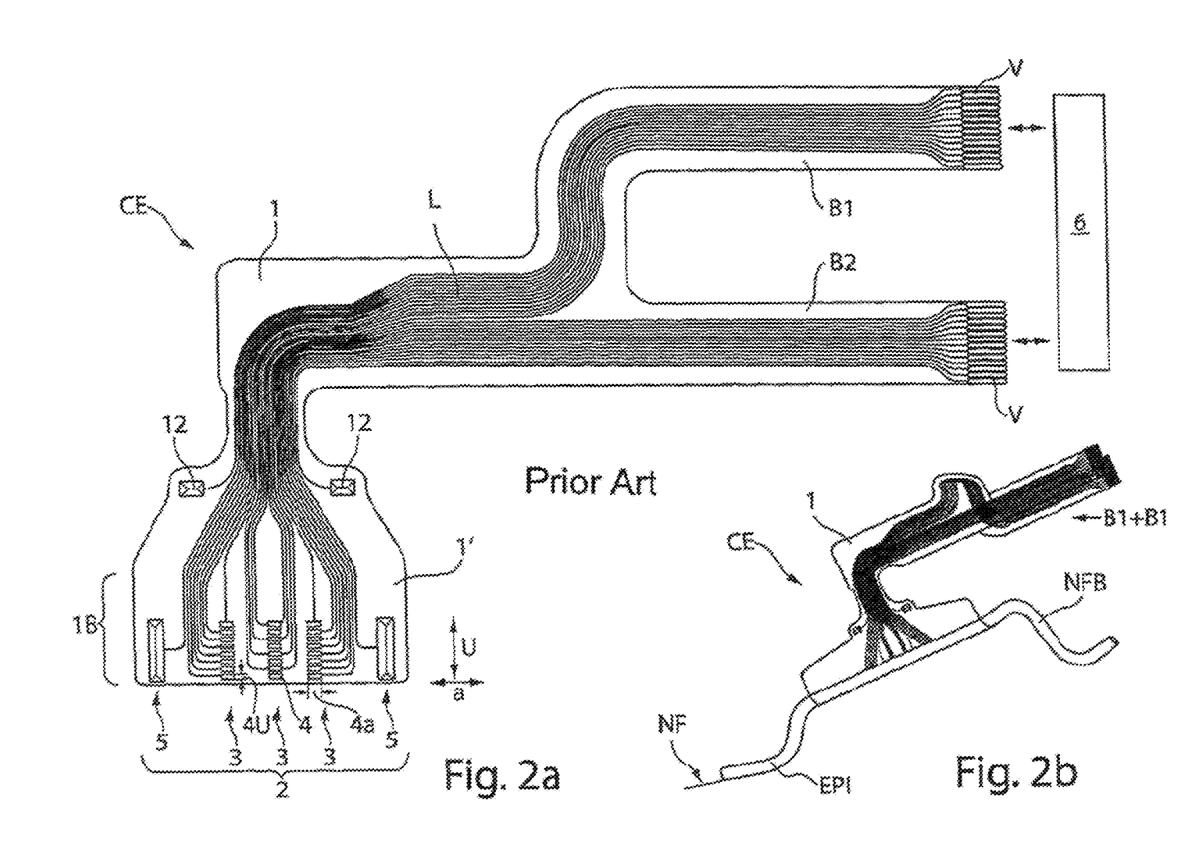

For the natural blood pressure regulation, the baroreflex is used, which constitutes a homeostatic, self-regulating mechanism and in the case of increased blood pressure activates different effectors by way of reflex. Among other things, the heart rate is reduced, but the arterial vessels are also expanded so as to thus lower the blood pressure. In the case of a low blood pressure, the baroreflex is suppressed, whereby the heart rate rises and blood vessels are constricted so that the blood pressure rises again. The sensory inputs for the baroreflex constitute what are known as baroreceptors, which are disposed, inter alia, in the walls of the aortic arch. From there, the blood pressure information travels monosynaptically along the nerve fibers relevant for blood pressure, referred to hereinafter as baroreceptive fibers, into the brainstem. When a threshold value for the blood pressure is exceeded, the baroreflex triggers an inhibition of sympathetic nerve fibers, which leads to an immediate lowering of the blood pressure. With the aid of the sleeve electrode illustrated with reference to FIGS. 2a and b, which is often referred to in the English-language literature as a cuff electrode, it is possible to use this baroreflex mechanism by selectively detecting the pressure information supplied to the brainstem and also selectively "overwriting" this information in order to thus suggest a significantly increased blood pressure situation to the brainstem, whereby a natural significant blood pressure lowering is initiated.

FIG. 2a shows the known cuff electrode CE in a two-dimensional plan view in a planar unfolded state. FIG. 2b shows the cuff electrode CE in the implanted state, in which regions B1, B2 of the cuff electrode CE have been folded together for the purpose of providing a space-saving form, and in addition a carrier substrate region 1B of the cuff electrode CE provided with an electrode arrangement 2 surrounds a region of a nerve fascicle NFB in a sleeve-like manner.

The cuff electrode CE has a flexible, biocompatible carrier substrate 1, which in the provided embodiment is a polyimide film approximately 11 μm thick. An electrode arrangement 2, composed of a multiplicity of individual electrodes, is applied to the carrier substrate upper side of the carrier substrate, facing towards the drawing plane in FIG. 2a, for the purpose of spatially resolved detection of neuronal electrical signals and also for selective electrical stimulation of individual nerve fibers NF running in the nerve fascicle NFB. The individual electrodes of the electrode arrangement 2 are in direct surface contact with the epineurium EPI of the nerve fascicle NFB, since the carrier substrate 1 in the carrier substrate region 1B rolls up automatically as a result of appropriate impression of a mechanical film bias, so as to form an oriented straight cylinder-shaped carrier substrate surface 1' facing the nerve fascicle NFB, as can be seen in FIG. 2b. The individual electrodes of the electrode arrangement 2 thus assume an annular three-dimensional form curved around the nerve fascicle NFB in the circumferential direction U.

Three first electrode structures 3, which are spaced apart from one another equally in the axial direction and which in the circumferential direction U in each case comprise at least two, and in the illustrated exemplary embodiment according to FIGS. 2a and b, eight first electrode surfaces 4 are used both for spatially-selective detection of neuronal electrical signals and for selective electrical stimulation of at least one nerve fiber NF. The eight first electrode surfaces 4 belonging in each case to a first electrode structure 3 are arranged equally distributed in the circumferential direction U, that is at angular intervals of 45°. This enables a spatial selectivity divided eightfold in the circumferential direction for spatially-selective detection of neuronal electrical signals from the nerve fascicle NFB to be examined. The first electrode strips 5 are arranged axially on both sides next to the three first electrode structures 3. The strips surround the nerve fascicle NFB fully in an annular manner and serve in the case of the spatially-selective detection of neuronal electrical signals as ground potential. If, by contrast, it is necessary to selectively electrically stimulate selected nerve fibers NF within the nerve fascicle NFB, these first electrode strips 5 each serve as anode or as opposite polarity.

The triple or tripole arrangement of the first electrode structures 3, via the first electrode surfaces 4 for detectors neuronal electrical signals or for delivering electrical signals for the purpose of spatially-selective stimulation. This makes it possible to determine impedance changes on account of tissue growth at the metal electrode surfaces 4 and to eliminate these by way of analysis. On the other hand blood pressure-relevant neuronal signals which run through the tripole arrangement axially along a corresponding nerve fiber NF with a slight time offset can be detected by suitable tripolar amplification. The above-mentioned first electrode structures 3 and also first electrode strips 5 each assuming a ring shape, which are all applied to the carrier substrate surface 1' facing the drawing plane in FIG. 2a and which end on the proximal side at connection structures V via corresponding electrical conductive tracks L. Reference electrodes 12 are disposed on the rear side of the carrier substrate 1 and serve to detect the intracorporeal electrical background ground signal or noise level, which forms the basis of the signal evaluation, and on the other hand provides the possibility of detecting ECG signals with the aid of the cuff electrode CE. The electrode arrangement implantable as a cuff electrode CE is connectable via the electrical connection structures V to a hermetically encapsulated signal detector and generator 6, which is also formed as an implant.

With the known implantable electrode arrangement, it was possible to show, within the scope of animal tests on rats, that with the aid of the total of 24 first electrode surfaces arranged in a tripolar manner equally distributed about the fascicle NFB, neuronal electrical time signals (referred to hereinafter as baroreceptive signals) can be detected, which additionally serve to locate the baroreceptive nerve fibers on the basis of their circumferential direction-dependent signal level. The stimulation was performed in a tripolar manner in each case with the electrode surface 4 or the electrode surfaces 4 of the centrally arranged first electrode structure 3 of the tripole arrangement via which the greatest signal level from the baroreceptive signals was detected in each case during the detection. It was possible to show that, by selective stimulation of baroreceptive nerve fibers, the blood pressure can be significantly reduced, wherein merely a very slight bradycardia (pulse reduction below 60 beats per minute) and only an insignificant bradypnoea (reduction in breathing less than 20 breaths per minute) are experienced.

For selective electrical stimulation of the baroreceptive nerve fibers, electrical stimulation signals having a stimulation frequency in each case between 30 and 50 Hz, a stimulation period of from 0.1 to 0.5 msec, and also a stimulation amplitude of from 0.4 to 1.5 mA were applied to the selected electrode surfaces 4 of the centrally arranged electrode structure. Here, the electrical stimulation along the baroreceptive nerve fibers was isotropic, that is with no specification of a fixed signal propagation direction, and therefore the electrical stimulation signals could propagate along both afferent and efferent nerve fibers. The latter can exert a direct, uncontrolled influence on the heart activity, which can lead to undesirable side-effects, in particular in the case of living beings larger than rats.

SUMMARY OF THE INVENTION

The invention is an implantable electrode arrangement of the above-mentioned type for spatially-selective detection of neuronal electrical signals, which propagate along at least one nerve fiber contained in a nerve fascicle, and for selective electrical stimulation of the at least one nerve fiber with measures being taken to rule out (as completely as possible) any possible side effects caused by uncontrolled signal propagation effects of the electrical stimulation signals selectively coupled-in along baroreceptive nerve fibers. In particular, measures should be taken to suppress a propagation of electrical stimulation signals along efferent nerve fibers without, in so doing, exerting a significantly lasting influence on non-baroreceptive afferent and also efferent nerve fibers within the nerve fascicle.

The implantable electrode arrangement is characterised in that at least one second electrode arrangement is arranged next to the first electrode arrangement in the axial sequence on the straight cylinder-shaped carrier substrate surface facing the nerve fascicle. The second electrode arrangement comprises at least two second electrode strips, which are axially spaced apart from one another, extend in the circumferential direction and in each case have a ring shape, and at least one second electrode structure, extending axially between the at least two second electrode strips, in each case comprising at least two second electrode surfaces arranged equally distributed circumferentially, wherein the second electrode arrangement is connected at least with the signal generator or a further signal generator.

The implantable electrode arrangement explained in the introduction as being formed as a cuff electrode, as is explained with reference to FIGS. 2a and b, has been supplemented in accordance with the invention by at least one second electrode arrangement designed for inhibition of a unidirectional electrical signal transfer along at least one selected nerve fiber within a nerve fascicle.

The second electrode arrangement also applied to the same carrier substrate formed continuously in one piece on the same carrier substrate surface as the first electrode arrangement is in a spatially fixed arrangement relative to the first electrode arrangement, in particular relative to the first electrode surfaces of the at least three first electrode structures, with the aid of which baroreceptive nerve fibers within the nerve fascicle are detected in a spatially-selective manner and additionally can be electrically stimulated selectively. In the knowledge of the localized baroreceptive nerve fibers, the second electrode arrangement can be used for the purpose of a selective inhibition of the baroreceptive nerve fibers in order to suppress a forwarding of electrical stimulation signals along efferent nerve fibers, that is to say nerve fibers leading to the heart. For this purpose, at least two, and preferably four or more second electrode surfaces of at least one second electrode structure are used, which, similarly to the first electrode surfaces of one of the at least three first electrode structures, are arranged equally distributed circumferentially relative to the straight cylinder-shaped carrier substrate surface oriented facing the nerve fascicle. For the purpose of inhibition of localized efferent baroreceptive nerve fibers, at least one of the second electrode surfaces of the second electrode structure is electrically activated. This results in a targeted, temporally limited, selective inhibition of the efferent nerve fibers in question. Here, an electrical polarization field passes from the at least one activated, second electrode surface into the nerve fascicle and interacts primarily with the nerve fibers to be inhibited. In order to axially limit the electrical polarization field propagating into the nerve fascicle during the inhibition, second electrode strips are used, which in each case are attached to the second electrode structure axially on either side and in the implanted electrode constitute ring electrodes completely surrounding the nerve fascicles.

For the purpose of the inhibition of selective efferent nerve fibers, the implantable electrode arrangement formed in accordance with the invention is applied to the nerve fascicle in such a way that the second electrode arrangement provided in accordance with the invention is oriented facing the heart, or facing the baroreceptive receptors, that is caudally, and the first electrode arrangement, with which the selective detection of neuronal electrical signals and also the electrical stimulation of localized nerve fibers is performed, is oriented facing the brain, that is rostrally, along the nerve fascicle.

With the aid of the second electrode arrangement, the inhibition can be provided either by way of what is known as an anodal block or by application of sinusoidal signals having frequencies in the kilohertz range. In the case of the anodal block, at least one of the second electrode surfaces is anodically positively polarized, whereby a voltage potential prevailing at the location of the efferent nerve fibers is produced, by which an activating stimulation of the corresponding nerve fibers is suppressed. An inhibition by way of a high-frequency signal application can also be attained, in which case a high-frequency electrical inhibition signal is applied to at least one selected second electrode surface, whereby the electrical signal transfer mechanisms along the efferent nerve fibers come to a stop temporarily.

In both cases, on account of its spatially limited extent axially, which is caused by the axial spacing of both second electrode strips, and in spite of its spatial vicinity to the first electrode structure (the implantable electrode arrangement should nevertheless not exceed an axial length of 4 cm), the second electrode arrangement provided in accordance with the invention acts axially in a spatially limited manner along the efferent nerve fibers to be inhibited, such that the electrode arrangement arranged first along the nerve fascicle on the brain side can couple electrical stimulation signals leading to the brain into the localized afferent nerve fibers in a manner uninfluenced by the inhibition mechanism. In this way, any side effects caused by possible direct stimulation in the direction of the nerve fibers leading to the heart, that is efferent nerve fibers, can be excluded.

The second electrode surfaces of the second electrode structure are advantageously arranged equally distributed circumferentially along a virtual circular line in the implanted cuff electrode to thus selectively and effectively inhibit localized efferent nerve fibers relative to the circumferential edge of a nerve fiber fascicle.

The second electrode surfaces, however, advantageously are not necessarily formed identically to one another in terms of shape and size, wherein their axial extension are in each case selected identically. That is to say identical to the axial extension of the first electrode surfaces of the first three electrode structures. The extension of the second electrode surfaces oriented circumferentially is selected to be greater than the extension of the first electrode surfaces oriented in the circumferential direction. The second electrode surfaces thus preferably have a greater area dimension compared to the first electrode surfaces, whereby the location selectivity with which the second electrode surfaces can electrically polarize specific efferent nerve fibers is lower than the location selectivity with which the first electrode surfaces can electrically stimulate localized nerve fibers. Alternatively, the second electrode surfaces can also be formed as circular areas instead of having a rectangular shape. This has the advantage that no local electrical potential field peaks are caused by edges or corners.

The second electrode arrangement is preferably formed as a tripolar electrode arrangement. That is the second electrode structure is limited axially on either side in each case by an annular second electrode strip, wherein the axial distance between both second electrode strips along the carrier substrate is selected preferably to be between 0.5 cm and 3 cm, in particular between 0.75 cm and 1.25 cm. The annular second electrode strips preferably have an axial extent between 1 μm and 5 mm, preferably between 100 μm and 4,000 μm.

The second electrode surfaces of the second electrode structure are arranged axially centrally between both second electrode strips and have an axial extension such that the axial distance between the second electrode strips is in each case greater than their own axial extension.

In particular in view of the possibility of carrying out depolarizing measures, it is conceivable, instead of one second electrode structure, to arrange three axially spaced second electrode structures between the second electrode strips, to form the first electrode structure within the first electrode arrangement. It should be mentioned here, only for the sake of completeness, that it would also be conceivable to arrange more than three first and second electrode structures between the respective first and second electrode strips. Three, five, seven, or a greater odd number of first and/or second electrode structures could thus be provided.

In a preferred exemplary embodiment illustrated hereinafter, a second electrode structure comprises four second electrode surfaces, the electrode area dimension of which is in each case smaller than a quarter of the area of a second electrode strip. Since the first and second electrode strips provided in the first and second electrode arrangement serve in each case as ground or an opposite pole for polarization of the first and second electrode structure respectively, the areas of the first and second electrode strips must be selected identically for reasons relating to charge-symmetrical conditions. However, it is also conceivable to provide an individual, independent area selection when forming the first and second electrode strips.

It has also proven to be advantageous to manufacture all electrodes of the second electrode arrangement, that is the second electrode surfaces and second electrode strips, from an electrically conductive material which has a lower charge transfer capacity than the electrode material from which the first electrode surfaces of the first electrode arrangement are made. Iridium oxide is used as a particularly suitable material having a particularly high charge transfer capacity in order to form the first electrode surfaces of the first electrode arrangement, whereas the material of the second electrode surfaces and second electrode strips are platinum or of an electrically conductive polymer.

All electrode surfaces both of the first and second electrode arrangement are preferably formed flush with the carrier substrate surface of the carrier substrate or are lower by comparison therewith, such that they do not protrude beyond the carrier substrate surface, to produce the most gentle surface contact possible to the epineurium of the nerve fascicle. Due to the non-invasive surface contact, the implantable electrode arrangement can be easily applied and positioned along the nerve fascicle by a surgical operation, wherein the epineurium is irritated only minimally, or not at all.

In order to also counteract tissue irritation and sensitivity reactions caused by implantation, it is possible to provide the carrier substrate of a biocompatible polymer with an active substance inhibiting inflammatory reactions, at least in those regions which come into direct surface contact with the nerve fascicle. A further measure for reducing mechanical irritation of the nerve fascicle, which can be caused as a result of the surface contact with the sleeve-like cuff electrode, concerns a rounding of axial limiting edges of the carrier substrate surrounding the nerve fascicle, such that the biocompatible carrier substrate, in the region of the straight cylinder-shaped carrier substrate surface oriented facing the nerve fascicle, has edge regions in each case disposed opposite one another axially, at which the carrier substrate has a greater substrate thickness than in the other carrier substrate region, wherein the edge regions have rounded edges.

In the region of the second electrode arrangement, which serves for the electrical inhibition of localized nerve fibers, a further preferred embodiment provides at least one, and preferably a plurality of light wave conductor openings or apertures, via which light can be applied or coupled in through the epineurium of the nerve fascicle. The light wave conductor openings are preferably arranged axially adjacently to both second electrode strips and in terms of shape, size and distribution are emulated in a manner corresponding to the second electrode surfaces of the second electrode structure. By providing a plurality of spatially separated light wave conductors, which open out on the carrier substrate surface in a manner facing the nerve fascicle, uniform or different optical signals with different wavelengths can be applied to the nerve fascicle for the purpose of optically activating neuronal optogenetic reactions within the nerve fascicle. Neuronal activation or inhibition reactions can thus be triggered in a spatially-selective manner by a multiplicity of suitably arranged light wave exit openings or apertures within the nerve fascicle. These reactions can be performed alternatively or in addition to the neuronal processes caused via the electrode surfaces.

As already mentioned, the implantable electrode arrangement formed in accordance with the invention must be applied along the nerve fascicle in such a way that the second electrode arrangement comes to lie along the nerve fascicle in the direction facing the heart. It is ensured in this way that efferent nerve fibers can be inhibited, whereas the first electrode arrangement oriented facing the brain along the nerve fascicle can be used for the purpose of selective stimulation of localized afferent nerve fibers, which are nerve fibers leading to the brain. Should it be necessary to selectively inhibit afferent nerve fibers, the implantable electrode arrangement formed in accordance with the invention can be implanted with reverse orientation along the nerve fascicle. A further possible embodiment provides a second inhibiting second electrode arrangement, which is attached axially beside the first electrode arrangement, opposite the second electrode arrangement.

For actuation and electrical signal and power supply of all electrode surfaces and electrode strips applied to the carrier substrate, at least one signal detector and generator is provided, which together with an electrical power supply unit is hermetically closed separately from the carrier substrate within a capsule-like housing or is provided as an integral part of the carrier substrate. In the case that the signal detector and generator is formed separately, this is connectable via a corresponding electrical and possibly optical interface to the implantable electrode arrangement formed in accordance with the invention.

The intracorporeal implantation of the electrode arrangement surrounding the nerve fascicle in a cuff is additionally confronted by the fundamental problem that the electrode strips and electrode surfaces applied to the polyimide carrier substrate are exposed to a permanently moist environment, whereby signs of degradation can occur in particular at the planar connections between the electrode surfaces and the polyimide carrier substrate. This leads to local separations and to contact degradations associated at least therewith, as a result of which the electrical efficiency of the electrode arrangement ultimately is impaired. In order to confront the signs of separation between metal electrode surfaces and the polyimide carrier substrate caused by this environment, at least the first and second electrode strips in a preferred embodiment in each case have at least one local opening, wherein the first and second electrode strips are connected in a planar manner to the carrier substrate or the carrier substrate surface in such a way that the polymer or polyimide, from which the carrier substrate is formed, at least partially penetrates through an opening. An improved mechanical anchoring of the respective electrode strips to the carrier substrate is thus created.

A further possibility for a durable and stable connection between the electrode surfaces or electrode strips and the biocompatible polyimide or polymer material of the carrier substrate is reflected in a specific embodiment of the electrode surfaces or electrode strips, and also in a resultant possible special integration of the electrodes in the carrier substrate. For this purpose, the first and second electrode strips in particular in each case have a metal base plate with a flat upper side and lower side, with at least one, and preferably a plurality of structural elements protruding orthogonally and locally beyond the upper side of the base plate, which elements are preferably pillars, ribs, sleeves, or webs. The metal base plate is completely encased by the biocompatible polymer of the carrier substrate, with the exception of a first surface region of the at least one structural element, which is oriented facing the carrier substrate surface and does not protrude therebeyond. The electrode contact surface freely accessible at the carrier substrate surface thus reduces, but is completely encased by the biocompatible polymer of the carrier substrate on account of the hermetic encapsulation of the base plate and also the structural elements integrally connected thereto, with the exception of the surface regions oriented facing the carrier substrate surface. An infiltration of environment-induced liquid or moisture between the electrode strips and the biocompatible polymer of the carrier substrate is significantly hindered, such that signs of degradation can be largely ruled out. In a further preferred embodiment, an adhesion promoter layer or an adhesion promoter layer arrangement is preferably introduced between the lower side of the metal base plate and the biocompatible polymer of the carrier substrate and counteracts potential moisture-induced signs of separation.

Further preferred embodiments in relation to the possible design of the electrode strips will be explained in conjunction with the following figures.

BRIEF DESCRIPTION OF THE DRAWINGS

The invention will be described hereinafter by way of example, without limitation of the general inventive concept, on the basis of exemplary embodiments with reference to the drawings, in which:

FIGS. 2a and b show illustrations of a prior art implantable electrode arrangement, known per se, for the spatially-selective detection of neuronal electrical signals and also selective electrical stimulation of individual nerve fibers;

DETAILED DESCRIPTION OF THE INVENTION

Figure 1:
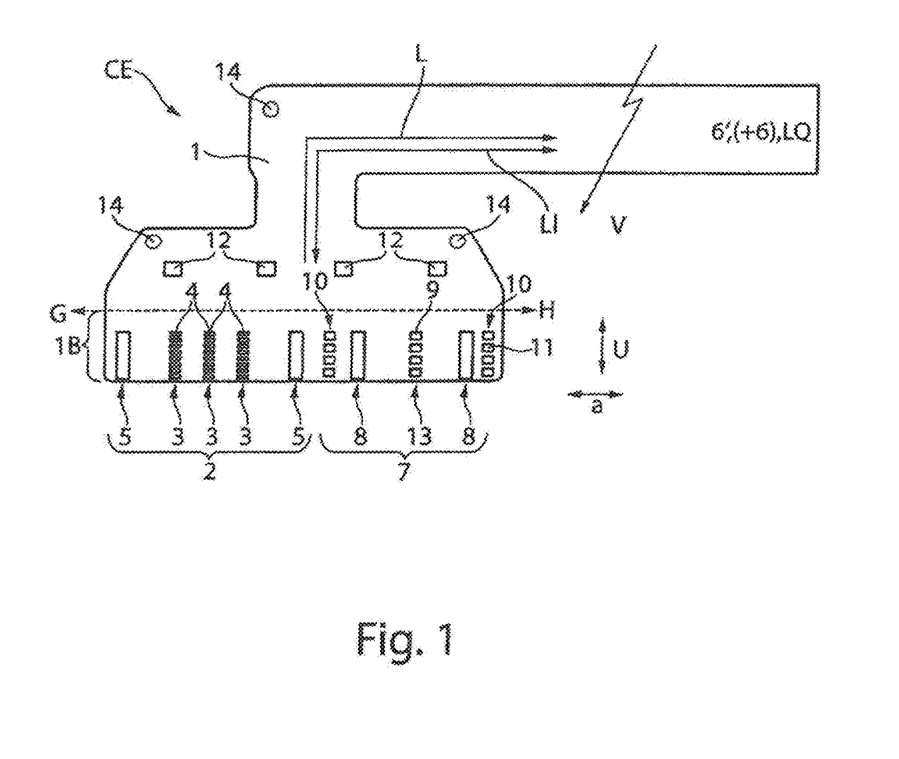
FIG. 1 shows a plan view of a schematic implantable electrode arrangement with a second electrode arrangement for the inhibition of selective nerve fibers.

FIG. 1 shows a schematic plan view of an implantable cuff electrode CE formed in accordance with the invention, with a second electrode arrangement 7 for the inhibition of at least one selective nerve fiber being applied to the carrier substrate 1 of the cuff electrode. The carrier substrate is preferably made of polyimide. In addition the first electrode arrangement 2 is provided for the spatially-selective detection of neuronal electrical signals and also for selective electrical stimulation of individual nerve fibers. The above description of FIGS. 2a and b with regard to the explanation of the individual electrodes of the first electrode arrangement 2 is incorporated by reference in its entirety.

The second electrode arrangement 7, for inhibiting the signal propagation along efferent nerve fibers, which here are nerve fibers leading to the heart H, comprises two axially spaced-apart second electrode strips 8, between which there is provided, centrally, a second electrode structure 13, which has four second electrode surfaces 9 arranged separately from one another. All electrodes 8 and 13 of the second electrode arrangement 2 are connected or connectable via electrical conductive tracks L applied to the carrier substrate 1 or integrated therein to a signal generator 6', which together with the signal detector and generator 6 and also with a power source is integrated in a separately encapsulated, implantable unit. The electrical conductive tracks L can optionally comprise a separable connection structure V.

The second electrode arrangement 2 optionally comprises light wave conductor arrangements 10, which in each case comprise four separate light wave conductor openings 11 distributed circumferentially in direction U. The light wave conductors LI run within the carrier substrate 1 to the individual light wave conductor openings or apertures 11 and can be combined proximally with a uniform light source LQ or with separate light sources LQ of different wavelengths so as to bring about optogenetically selectively activated stimulations and/or optically activated and selective inhibition along specific nerve fibers.

The geometric selection of the shape and size of the individual electrodes, that is of the first and second electrode strips 5 and 8 and also of the first and second electrode surfaces 4 and 9 can be made in principle in a manner coordinated individually with one another and is based in particular on the diameter of the nerve fascicle so as to be able to place the implantable cuff electrode CE in position. The extent of the first and second electrode structures and electrode strips oriented in the circumferential direction U and also possibly the optical light wave conductor arrangements 10 thus preferably corresponds to the circumferential edge of the nerve fascicle around which the cuff electrode CE is to be wound. The axial spacing of the tripolar electrode arrangement should preferably be adapted to the diameter and the resultant spacing of what are known as the nodes of Ranvier in myelinated nerve fibers of the nerve fibers to be excited. In the exemplary embodiment illustrated in FIG. 1, the electrodes are illustrated as rectangular electrode surfaces. It is advantageous to form the electrode surfaces at least with rounded corners, in particular for the purpose of avoiding field line densifications occurring at electrode rectangle corners.

In humans, it is necessary to inhibit or to activate specific, large and myelinated fibers. This is possible only at points along the nerve fibers at which these fibers are not myelinated, that is at what are known as nodes of Ranvier. With increasing diameter of the nerve fibers, the intervals, that is the axial distances between the nodes of Ranvier, become larger, and accordingly it is necessary to select the axial spacing between two axially distanced first electrode strips 5 to be approximately the same length as the axial spacing of the rings or slightly greater so as to also reach the nodes of Ranvier of very large fibers with sufficiently high statistical probability. The same is preferably also true for the axial spacing of the second electrode strips 8.

The axial total extent of the entire cuff electrode CE should be adapted to the intracorporeal proportions of the particular nerve fascicle and typically should not exceed 4 cm.

The additional reference electrode surfaces 12 attached to the carrier substrate 1 on the rear side serve to detect the noise level which is detectable intracorporeally, and thus ECG signals as necessary.

The carrier substrate 1 additionally has at least one and preferably two or three openings 14 which are strengthened by metal ring structures The openings serve to fasten the implanted electrode arrangement CE to the nerve fascicle. The fastening is provided with the aid of a surgical thread, which is threaded at least once through each of the openings 14 and is sewed in the tissue surrounding the nerve fascicle. In contrast to the region 1B of the carrier substrate rolled into a straight cylinder, to which the first and second electrode arrangements 2 and 7 are applied, such that they contact the surface of the epineurium of the nerve fascicle in the implanted state, the carrier substrate 1 adjoining the carrier substrate region 1B protrudes laterally from the nerve fascicle configured to be a flat lug and projects into the surrounding tissue. The metal ring structures 14 are intended to help mechanically reliably absorb the fastening forces acting along the surgical thread and to prevent damage to the carrier substrate caused by the thread cutting therein.

The second electrode arrangement 7 should be arranged along the nerve fascicle on the side H leading to the heart in order to wind the implantable electrode arrangement CE in a cuff-like manner around a nerve fascicle (not illustrated in greater detail). The second electrode arrangement 2 serving for selective detection and also for selective stimulation of localized nerve fibers is attached along the nerve fascicle on the brain side G.

Figure 3A:
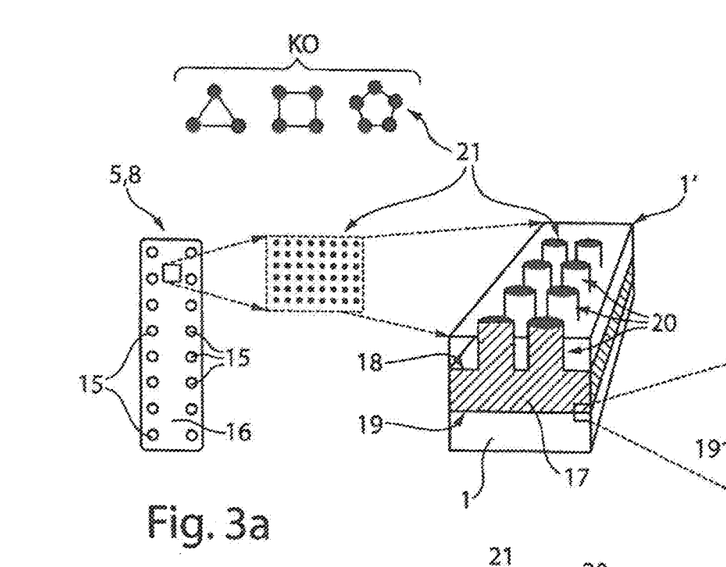
FIG. 3a shows an illustration of an electrode strip with opening.

The first and second electrode strips 5 and 8 and also the first and second electrode surfaces 4 and 9 are preferably applied to the carrier substrate by vapor deposition or sputtering but a galvanic reinforcement is conceivable. Laser structuring of thin metal foil is also a possible technique. For a permanent joining in particular of the first and second electrode strips 5 and 8, to the carrier substrate 1, the electrode strips have local openings 15 shown in FIG. 3*a*, through which the polymer material of the carrier substrate 1 passes or projects at least in part. The electrode surface 16 of the first and second electrode strips 5 and 8 are in each case for the remainder arranged flush with the carrier substrate upper side 1' and directly contact the surface of the nerve fascicle.

Figure 3B:
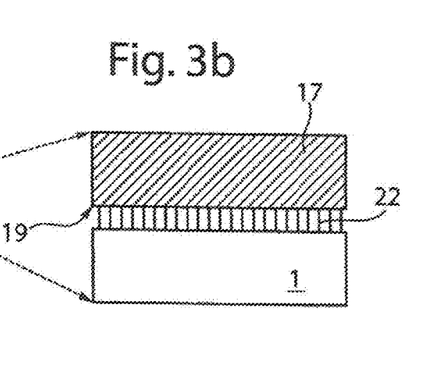
FIG. 3b shows a detailed illustration of an electrode strip integrated in the carrier substrate.

In order to permanently improve the joining of the electrode strips 5 and 8, it is proposed in a preferred exemplary embodiment to integrate the electrode strips largely into the carrier substrate in the following way as shown in FIG. 3*b*.

The electrode strips 5 and 8 in each case have a metal base plate 17, having an upper side 18 and a lower side 19. Orthogonally raised structural elements 20 are provided integrally with the upper side 18 of the base plate 17, which are distributed in a planer over the surface of the upper side 18. Preferably the raised structural elements 20 are distributed over the entire surface of the upper side, preferably in the form of a pillar, rib, web, or sleeve extensions, which have a surface region 21 facing the carrier substrate surface 1'. The surface region can be in direct contact with the epineurium of the nerve fascicle. In addition, an adhesion promoting layer 22 is advantageously provided at least between the lower side 19 and the polymer material of the carrier substrate 1 surrounding the base plate 17. The adhesion promoting layer 22 can additionally also be applied to the upper side 18. Particularly suitable adhesion promoting layers are silicon carbide (SiC) and also diamond-like carbon (DLC). The electrode strips 5 and 8 are preferably manufactured from iridium oxide, which is a material having one of the highest charge transfer capacity.

Figure 3C:
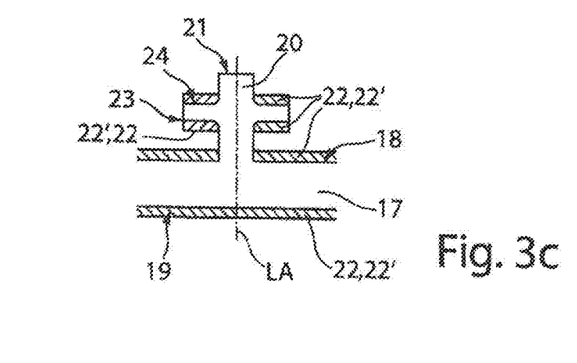
FIG. 3c shows an alternative design of a structural element.

A further improved variant for forming the structural elements 20, which are applied in a distributed manner to the upper side of the base plate 17, is illustrated in FIG. 3*c*. FIG. 3*c* shows the longitudinal section through a structural element 20 which has a longitudinal extent LA oriented orthogonally to the upper side 18 of the metal base plate 17, along which the structural element 20 has at least one second surface region 23, which is oriented parallel to the upper side 18 of the metal base plate 17 and to which the adhesion promoting layer 22 or an adhesion promoting layer arrangement 22' is applied. The second surface region 23 is fully surrounded by the biocompatible polymer in a manner arranged at a distance and separated from the first surface region 18 by the first adhesion promoting layer (22) or the adhesion promoting layer arrangement (22'). As can be inferred from FIG. 3*c*, the second surface region is oriented facing the upper side 18 of the base plate 17 and it is additionally possible and advantageous to provide the adhesion promoting layer 22 or the adhesion promoting layer arrangement 22' both on a third surface region 24, which is opposite the second surface region 23, and/or on the upper side and/or lower side 18 and 19 of the base plate 17.

The number and also arrangement of the individual structural elements 20 can be selected arbitrarily, but geometrically ordered in constellations KO, such as square, pentagonal, hexagonal or higher-value arrangement patterns, which are preferably suitable, as is understood from FIG. 3*b*.

In a preferred arrangement of the base plate 3 within the carrier substrate 1, the base plate 17 is disposed centrally within the carrier substrate 1 that is the thickness of the biocompatible polymer layer bordering the lower side 19 of the base plate 17 should correspond approximately to the thickness of the polymer layer bordering the upper side 18 of the base plate 17. With this arrangement of the base plate 17, there is provided the advantage, which can be demonstrated by way of experiments, that the inherent metal stresses acting on the base plate 17 and which form during a tempering process are compensated. The tempering process is necessary in order to impress a material bias into the carrier substrate, by which the implantable cuff electrode can wind autonomously around the nerve fascicle.

FIG. 4*a* to *f* illustrate a cuff M which partially surrounds the carrier substrate 1 of the implantable cuff electrode CE and which surrounds the region of the carrier substrate 1, both on the lower side and also upper side thereof, that directly adjoins the carrier substrate region 1B and, in contrast to the carrier substrate region 1B, does not deform independently in a straight cylinder-shaped manner by way of inherent material mechanical bias and in this way is made to be flush against the epineurium of the nerve fascicle in the implanted state.

The cuff M primarily serves to provide improved handling of the implantable cuff electrode CE, which on account of its very small carrier substrate thickness and also the filigree electrode arrangements applied to the carrier substrate surface, requires particularly careful handling on the part of the surgeon. The cuff M is preferably formed in one part and has a cuff lower part Mu and a cuff upper part Mo, which are both connected in a hinged manner via a living hinge joint 25 as shown as FIGS. 4b and 4c. The cuff lower part Mu has an indentation 26 in which the carrier substrate 1 is embedded and into which the carrier substrate 1 can be inserted. In the inserted state, the cuff lower part Mu comprises the carrier substrate 1 in the framing manner deducible from FIG. 4b, that is the cuff lower part Mu protrudes laterally beneath the carrier substrate 1.

Figure 4A:
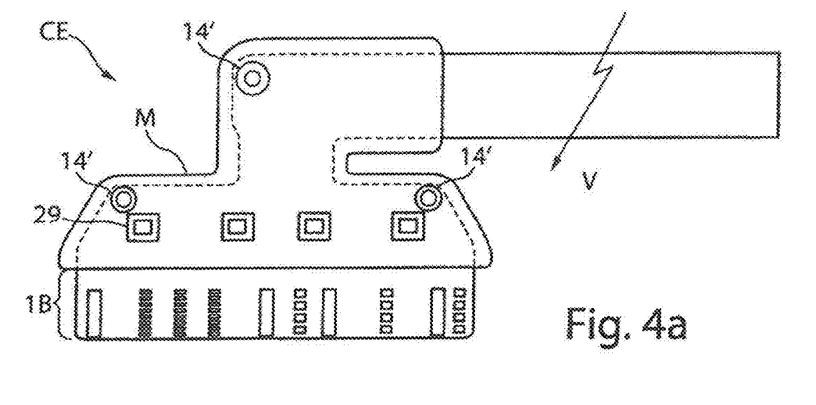
FIGS. 4a-f show illustrations of a cuff additionally strengthening the implantable electrode arrangement.

The cuff upper part Mo connected integrally to the cuff lower part Mu via the hinge joint 25 is adapted in terms of shape and size to the cuff lower part Mu and, similarly to the cuff lower part Mu, which has an indentation 27 in which the carrier substrate 1 is embedded, so that in the closed state the cuff M encases the carrier substrate 1 hermetically in the manner illustrated in FIG. 4a, wherein merely the carrier substrate region 1B protrudes from the cuff M.

Figure 4B:
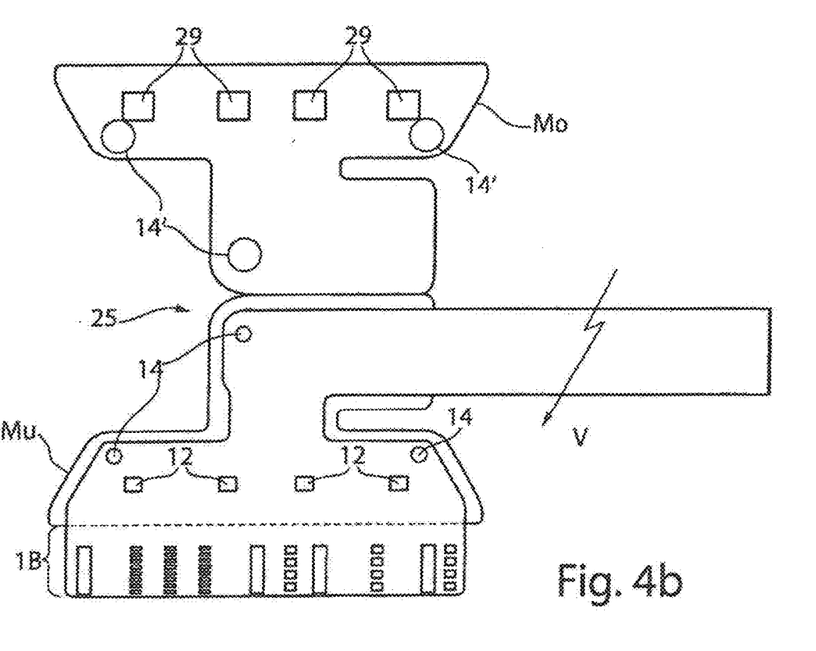

In addition to improved handling, the cuff M in particular also provides an improved fixing of the cuff electrode CE relative to the nerve fascicle. For this purpose, the cuff upper and lower sides Mo, Mu in each case provide fastening openings 14' as shown in FIGS. 4a, b and d, which, when the cuff M is folded together, are aligned with the fastening openings 14 formed within the carrier substrate 1. In this way, it is possible to guide a surgical thread 28 through the openings 14 and 14' in the cuff electrode CE surrounded by the cuff M. The fastening opening 14 of the cuff electrode CE, which is surrounded by a metal ring, can thus be relieved by the fastening opening 14' formed within the cuff M. The cuff M is preferably manufactured from a stable plastic material, which for example may be parylene. In order to further increase the strength, Mo and Mu can also be a polymer hybrid (for example parylene (internally) and silicone rubber (externally)). This hybrid has the advantage that the stability of parylene is combined with the tear resistance of the silicone. In a preferred embodiment, the fastening openings 14' within the cuff M are reinforced by an appropriate material thickening.

Opening windows 29, which ensure free access to the reference electrode surfaces 12, are formed in the cuff upper part Mo. FIG. 4e is a cross-section through the carrier substrate 1. The carrier is comprised of the cuff M on the upper side of reference electrode surfaces 12. The electrode surfaces remain freely accessible through the opening windows 29 formed within the cuff upper part Mo. The opening windows 29 preferably comprise the reference electrode surfaces 12 with a limiting flank 29' falling away in a sloped manner, which ensures that the reference electrode surfaces 29 can come into body contact with surrounding tissue over the entire surface.

Figure 4C:
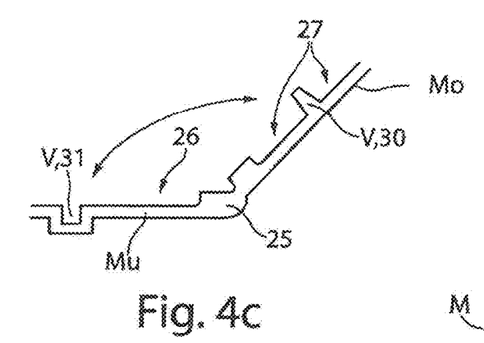
Figure 4D:
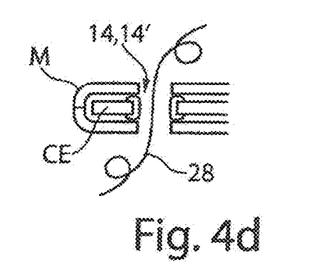
Figure 4E:
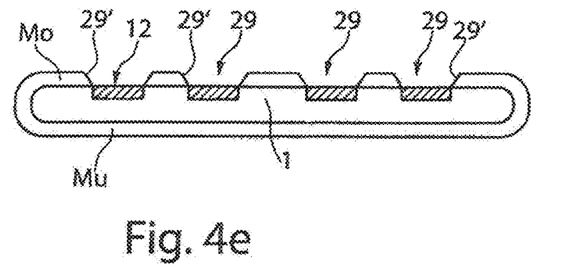
Figure 4F:
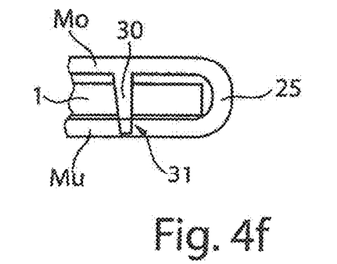

In order to ensure that the cuff M remains in a closed state, locking structures V are arranged between the cuff upper part and lower part Mo, Mu and for example are a pin 30 and indentation 31 arranged oppositely as shown in FIGS. 4c and f. When the cuff upper part and lower part are folded together, the pins 30 engage in the corresponding indentation 31 in a manner acted on by a force, which ensures that the pins 31 are held in place permanently in each case in a frictionally engaged manner. The closed state of a locking structure V is illustrated in FIG. 4f. Here, the pin 30, which is attached to the cuff upper part Mo, protrudes through a corresponding opening formed in the carrier substrate 1 and leads at the end into the indentation 31 of the cuff lower part Mu. Of course, alternative embodiments for the locking structures are conceivable, which for example may be in the form of suitably embodied latching mechanisms.

Figure 5:
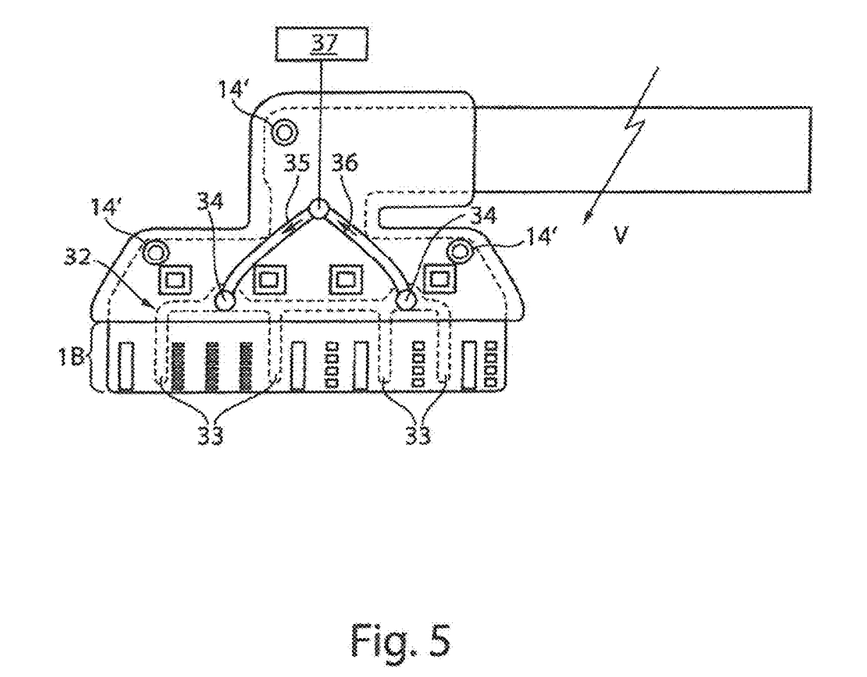
FIG. 5 shows hydraulic application structures of the implantable electrode arrangement.

FIG. 5 illustrates a further embodiment which enables a facilitated implantation of the cuff electrode CE formed in accordance with the invention. A fluid channel system 32 is formed within the carrier substrate 1 and is comprised fully by the carrier substrate 1. The fluid channel system 32 extends substantially in the region of the carrier substrate region 1B, which, on account of a material-inherent bias, assumes the form of a straight cylinder by way of an autonomous self-rolling, without the application of external force. If, by contrast, the fluid channel system 32 is filled with a fluid, which is preferably water, the water pressure forming along the fluid channel system 32 can thus cause the carrier substrate region 1b to spread out in a planar manner, against the material-inherent rolling forces. For this purpose, the fluid channel system 32 has fluid channel branches 33, which run in the circumferential direction of the lateral surface of the autonomously-forming straight cylinder and which, in the filled state, force the necessary extension of the carrier substrate region 1B.

In order to fill the fluid channel system 32, at least two channel openings 34 are provided within the carrier substrate 1. The size and arrangement of the openings are such that they open out in a fluid-tight manner at entry and exit openings of fluid feed and discharge lines 35 and 36 running within the cuff M. The feed and discharge lines 35 and 36 running within the cuff M and are fluidically connected to a fluid control system 37, which can be actuated by a surgeon.

In the case of an implantation, the fluid channel system 32 is filled with a fluid, whereby the carrier substrate region 1B is stretched out. In this state, the surgeon places the cuff electrode CE in a precise manner at a predefined point along the nerve fascicle. The fluid channel system 32 is then emptied by the surgeon, whereby the carrier substrate region 1B autonomously winds around the nerve fascicle. As a last step, the cuff electrode CE is fixed using a surgical thread to the surrounding tissue by the fastening openings 14' provided in the cuff.

In an advantageous embodiment of the above fluid channel system 32, it is possible to fill the fluid channel system with a shape-memory metal and shape-memory polymer. For the purpose of activation, the channel openings 34 are provided with metallized contacts, via which an electrical voltage can be applied along the feed lines 35 and 36 in order to unfold the implantable electrode arrangement CE via an accordingly modified control apparatus 37, until the electrode is ultimately placed in position.

REFERENCE LIST 1 carrier substrate
1' carrier substrate surface
1B carrier substrate region
2 first electrode arrangement
3 first electrode structures
4 first electrode surfaces
4a axial extent of the first electrode surfaces
4U extent of the first electrode surfaces oriented in the circumferential direction
5 first electrode strips
6, 6' signal detector and generator
7 second electrode arrangement
8 second electrode strips
9 second electrode surfaces
9a axial extent of the second electrode surfaces 9U extent of the second electrode surfaces oriented in the circumferential direction
10 light wave conductor arrangement
11 light wave conductor openings
12 reference electrode surfaces, ECG electrode surfaces
13 second electrode structure
14 fastening openings
14' fastening opening
15 opening
16 electrode strip surface
17 base plate
18 upper side
19 lower side
20 structural element
21 surface region
22 adhesion promoting layer
22' adhesion promoting layer arrangement
23 second surface region
24 third surface region
24 third surface region
25 living hinge joint
26 indentation
27 indentation
28 surgical thread
29 opening window
29' delimitation flank
30 pin
31 indentation
32 fluid channel system
33 fluid channel branches
34 channel opening
35 feed line, within the cuff
36 discharge line, within the cuff
37 fluid control system
CE cuff electrode
L conductive track
V connection structure
U circumferential direction
A axial direction
M cuff
Mo cuff upper part
Mu cuff lower part
1. NF nerve fiber
NFB nerve fascicle
G brain
H heart
LI light wave conductor
LQ light source(s)
LA longitudinal axis of the structural element
KO geometric constellations
V locking structure

The invention claimed is:

1. An implantable electrode for spatially selective directional detection and manipulating of neuronal electrical signals, which propagate along at least one nerve fiber contained in a nerve bundle, the nerve bundle including at least one nerve fiber of the nerve bundle leading neuronal signals in an afferent direction along at least one nerve fiber of the nerve bundle and at least one nerve fiber of the nerve bundle leading neuronal signals in an opposite efferent direction along the at least one nerve fiber of the nerve bundle, and which when implanted provides selective directional electrical overwriting of the at least one afferent nerve fiber in the afferent direction and also provides selective directional blocking of the at least one efferent nerve fiber in the efferent direction, comprising:

a biocompatible carrier substrate, including at least one carrier substrate region, comprising a cuff which is configured to be placed around the nerve bundle when implanted, including a cylindrical carrier substrate which is configured when implanted to be oriented to face the nerve bundle, a circumferential extension and an axial extension;

a first electrode attached to the biocompatible carrier substrate including at least three axially spaced first electrodes each comprising at least two first circumferential electrode surfaces, at least two separated axial first electrode strips which are configurable when implanted to assume a ring shape surrounding the nerve bundle to axially enclose the at least three first electrodes on both sides, and the first electrode is connectable or is connected to a signal detector and to a signal generator and configured when implanted to spatially selectively directionally detect the neuronal signals which propagate along the at least one nerve fiber leading in one of the efferent direction or the afferent direction contained in the nerve bundle and means configured, when implanted, for selectively overwriting the neuronal electrical signals flowing along at least one nerve fiber leading in the afferent direction to provide the directional electrical stimulation of the selected at least one nerve fiber leading in the afferent direction when connected to the signal detector and to the signal generator; and at least one second electrode attached to the carrier substrate and spaced from the first electrode which is configured, when implanted, to face the nerve bundle including at least two separated second annular shaped electrode strips extending axially between the at least two second electrode strips, each second electrode being configured when implanted to have at least two equally circumferentially spaced second electrode surfaces, and means configured, when implanted, for selectively inhibiting a selected at least one nerve fiber leading in the efferent direction when connected to the signal generator or to another signal generator.

2. The implantable electrode according to claim 1, wherein:
the surfaces of first and second electrodes are configured when implanted to be equally circumferentially distributed.

3. The implantable electrode according to claim 1, wherein:
the surfaces of first and second electrodes have an axial extension and a circumferential extension;
the extension of the first electrode surfaces are identical;
the extension of the second electrode surfaces are identical; and
the circumferential extensions of the second electrode surfaces are greater than the circumferential extensions of the first electrode surfaces.

4. The implantable electrode according to claim 1, wherein:
the axial extensions of the first and second electrode surfaces are identical.

5. The implantable electrode according to claim 1, wherein:
the biocompatible carrier substrate has a surface having the first and second electrodes applied thereto and the carrier substrate surface is a continuous single piece.

6. The implantable electrode according to claim 1, comprising:

an axial space between the first electrode strips which is equal to or greater than an axial space between the second electrode strips; and an axial spacing between the second electrode strips is between 0.5 cm and 3 cm.

7. The implantable electrode according to claim 6, wherein the axial space between the second electrode strips is between 0.75 cm and 1.25 cm.

8. The implantable electrode according to claim 1, wherein:

a shape and size of the annular shaped first and second electrode strips is identical; and an area of the first and second electrode surfaces is smaller than an area of the first or second electrode strips.

9. The implantable electrode according to claim 8, wherein an area of the first electrode surfaces is less than one quarter of an area of the first or second electrode strips.

10. The implantable electrode according to claim 1, wherein:

the first electrode surfaces are metallic and have a higher charge transfer capacity than a material from which the second electrode surfaces are made.

11. The implantable electrode according to claim 10, wherein:

the first electrode surfaces comprise iridium oxide; and
the second electrode surfaces are either metallic or are an electrically conductive polymer.

12. The implantable electrode according to claim 1, comprising:

at least one optical waveguide which is part of the second electrode and comprises at least two circumferentially distributed light wave conductor openings.

13. The implantable electrode according to claim 10, wherein:

the at least two circumferentially distributed light wave conductor openings are equally distributed; and the light wave conductor openings include an axial and circumferential extension corresponding to an axial and circumferential extension of the second electrode surfaces.

14. The implantable electrode according to claim 1, wherein:

the first and second electrodes comprise a tripolar electrode arrangement and when polarized the first and second electrode strips have a polarity opposite to a polarity of the first and second electrodes.

15. The implantable electrode according to claim 1, wherein:

the first electrode surfaces and the first electrode strips of the first electrode and the second electrode surfaces and the second electrode strips of the second electrode are configured to be implanted to be attached to but to not protrude beyond the carrier substrate surface.

16. The implantable electrode according to claim 1, wherein:

the carrier substrate comprises at least one biocompatible polymer comprising an active substance which is configured to inhibit inflammation reactions when implanted at least in regions on the cylindrical carrier substrate surface which is configured to be implanted to face the nerve bundle.

17. The implantable electrode according to claim 1, wherein:

the signal detector, the signal generator or another signal generator, and an electrical power supply unit are hermetically enclosed separately from the carrier substrate within a housing or are integral parts of the carrier substrate.

18. The implantable electrode according to claim 1, wherein:

the biocompatible carrier substrate comprises a biocompatible polymer.

19. The implantable electrode according to claim 18, wherein:

at least one of the first and second electrode strips has at least one opening, and at least one of the first and second electrode strips is connected in a planar configuration to the biocompatible carrier substrate with the biocompatible polymer to penetrate through the at least one opening.

20. The implantable electrode according to claim 18, wherein:

at least one of the first and second electrode strips has a metal base plate having a flat upper side and a flat lower side and at least one structural element protrudes orthogonally beyond the flat upper side;

the flat upper and lower sides of the metal base plate are parallel to the carrier substrate surface; and the metal base plate is encased by the biocompatible polymer except for a first surface region of the at least one element, faces the carrier substrate surface and does not protrude there beyond.

21. The implantable electrode according to claim 20, wherein:

the at least one structural element comprises identical multiple structural elements which are disposed on a flat upper side of the metal base plate in a pattern.

22. The implantable electrode according to claim 20, comprising multiple structure elements which protrude orthogonally beyond the flat side and include a pillar, a rib, a sleeve or a web.

23. The implantable electrode according to claim 20, comprising:

at least one structural element having a longitudinal extension oriented orthogonally to an upper side of the metal base plate and along the longitudinal extension of the at least one structural element and includes at least one second surface region parallel to the upper side of the metal base plate and to which an adhesion or an adhesion layer is applied; and the at least one second surface region is spaced from the first surface region and is surrounded by the biocompatible polymer.

24. The implantable electrode according to claim 1, wherein:

at least two reference electrode surfaces are attached to a rear side of the biocompatible carrier substrate.

25. The implantable electrode according to claim 1, wherein:

the biocompatible carrier substrate includes a second region having a straight cylindrically-shaped surface which is configured when implanted to face the nerve bundle and edge regions axially disposed opposite one another, and in the edge regions the biocompatible carrier substrate has a greater substrate thickness than all other carrier substrate regions; and the edge regions have rounded edges.

26. The implantable electrode according to claim 1, wherein:

the at least one carrier substrate region is configured, when implanted, to be placeable in the cuff around the nerve bundle and has at least one fastening opening which fully penetrates the biocompatible carrier substrate.

27. The implantable electrode according to claim 26, wherein:
the at least one fastening opening is surrounded by metal.

28. The implantable electrode according to claim 20, wherein:
the first surface region of the at least one structural element or a plane associated with the first surface region is parallel to the carrier substrate surface, is accessible from sides of the carrier substrate surface and the at least one structural element is integrally connected to the metal base plate.

29. The implantable electrode according to claim 20, wherein:
an adhesion layer is placed between at least the flat lower side of the metal base plate and the biocompatible polymer of the carrier substrate.

30. The implantable electrode structure according to claim 27, wherein:
the cuff of the biocompatible carrier substrate has an upper side and a lower side connected by a hinge; and
the upper side and the lower side each have fastening openings which are congruent to fastening openings of the carrier substrate and are configured to be disposed in the cuff of the carrier substrate when implanted.

31. The implantable electrode according to claim 1, wherein:
the cuff of the substrate surrounds the carrier substrate at least in a region and the biocompatible carrier substrate does not contain the carrier substrate surface.

* * * * *